US006757293B1

(12) United States Patent
Chuah et al.

(10) Patent No.: US 6,757,293 B1
(45) Date of Patent: Jun. 29, 2004

(54) METHODS AND APPARATUS FOR PROVIDING SHORT RACH FRAMES FOR FAST LATENCY

(75) Inventors: Mooi Choo Chuah, Eatontown, NJ (US); On-Ching Yue, Middletown, NJ (US); Qinqing Zhang, Matawan, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/203,932

(22) Filed: Dec. 2, 1998

(51) Int. Cl.$^7$ ................................. H04J 3/16
(52) U.S. Cl. .................. 370/432; 370/437; 370/438; 370/442; 370/458; 370/462; 370/470
(58) Field of Search ................. 370/352, 432, 370/433, 437, 438, 442, 443, 458, 462, 470, 471

(56) References Cited

U.S. PATENT DOCUMENTS

| | | | |
|---|---|---|---|
| 4,542,499 A | | 9/1985 | Bella et al. |
| 5,123,029 A | * | 6/1992 | Bantz et al. ................. 375/133 |
| 5,644,576 A | * | 7/1997 | Bauchot et al. ............. 370/437 |
| 5,751,702 A | * | 5/1998 | Evans et al. ................. 370/314 |
| 5,822,311 A | | 10/1998 | Hassan et al. |
| 5,991,633 A | * | 11/1999 | Corriveau et al. .......... 455/466 |
| 6,094,429 A | * | 7/2000 | Blanchette et al. ......... 370/347 |
| 6,097,704 A | * | 8/2000 | Jackson et al. ............. 370/280 |
| 6,181,683 B1 | * | 1/2001 | Chevillar et al. ........... 370/329 |
| 6,381,229 B1 | * | 4/2002 | Navinger et al. ........... 370/328 |
| 6,597,675 B1 | * | 7/2003 | Esmailzadeh et al. ...... 370/335 |

FOREIGN PATENT DOCUMENTS

| WO | WO 98/18280 | 4/1998 |
|---|---|---|
| WO | WO 98/35522 | 8/1998 |

OTHER PUBLICATIONS

E. Dahlman et al., "UMTS/IMT–2000 Based on Wideband CDMA," IEEE Communications Magazine, pp. 70–80, Sep. 1998.

ETSI SMG2/UMTS L2 & L3 Expert Group, "MS–UTRAN Radio Interface Protocol Architecture; Stage 2," Tdoc SMG2 UMTS–L23 172/98, Sep. 1998.

ETSI SMG2/UMTS Physical Layer Expert Group, "UTRA Physical Layer Description FDD Parts," Tdoc SMG2 UMTS–L1 221/98, vol. 4, Jun. 1998.

ETSI SMG2/UMTS L2 & L3 Expert Group, "Modification of the Current RACH Scheme for Increased Throughput," Tdoc SMG2 UMTS–L1 455/98, pp. 1–5, Oct. 1998.

\* cited by examiner

Primary Examiner—Steven H. D Nguyen
Assistant Examiner—Roberta Stevens

(57) ABSTRACT

The present invention provides an improved RACH access burst arrangement and frame structure. That is, the invention provides methods and apparatus for supporting more than one access burst length in the UMTS access channel structure. Preferably, two access burst lengths are supported, e.g., 5 ms and 10 ms. Such an arrangement is advantageous in applications where it is beneficial to have fast access latency such as, for example, voice or other forms of real-time traffic. Also, the invention provides methods and apparatus for supporting multiple frame sizes. It is to be appreciated that further enhancement to access latency can be obtained by having the UMTS physical layer support multiple frame sizes. The access burst signal transmitted by a remote terminal over the RACH may be an access request or data packets in the case where the RACH is being utilized for UMTS short message services.

36 Claims, 14 Drawing Sheets

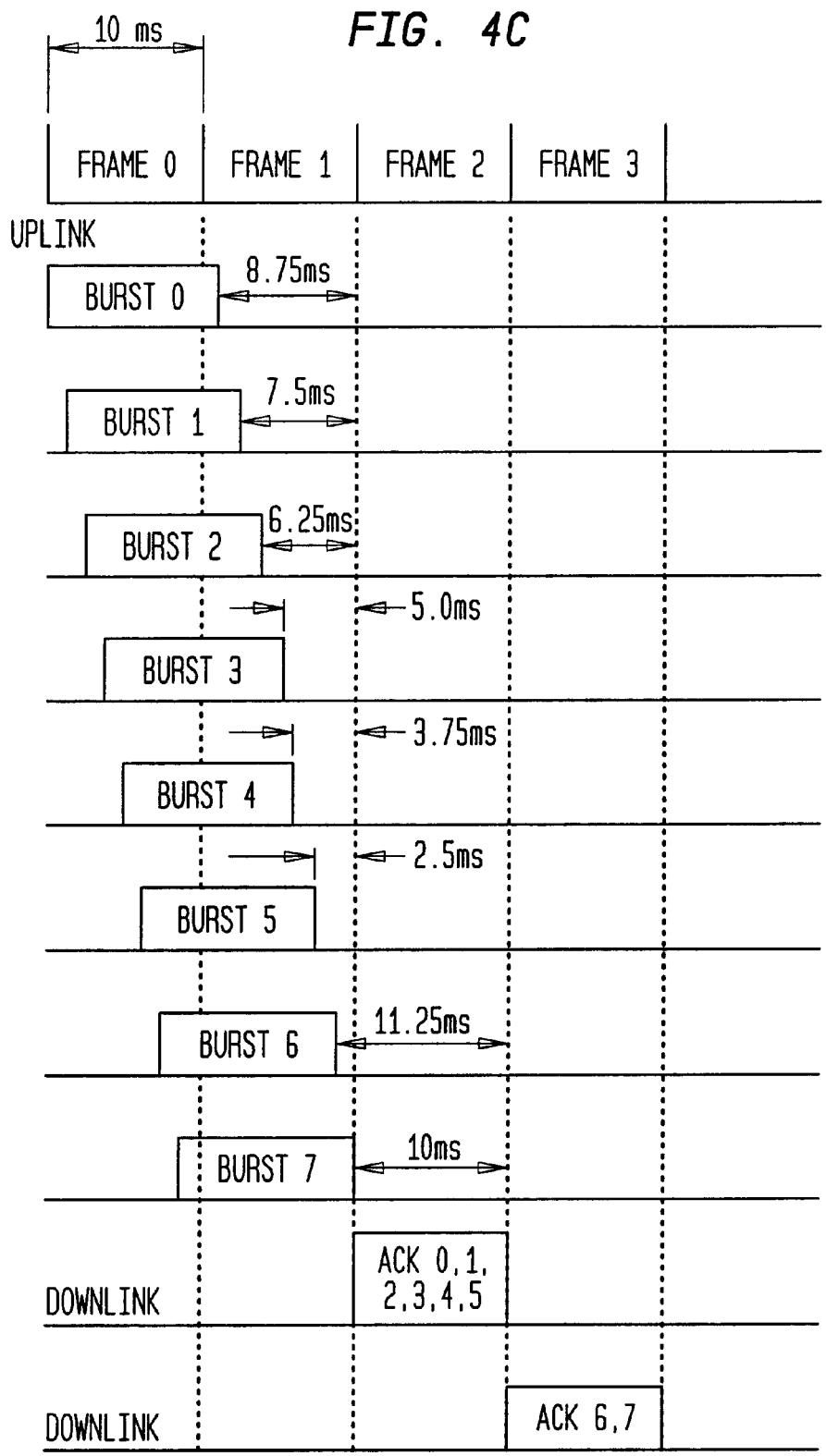

METHODS AND APPARATUS FOR PROVIDING SHORT RACH FRAMES FOR FAST LATENCY

CROSS REFERENCE TO RELATED APPLICATIONS

This application is related to the U.S. patent application identified as Ser. No. 09/203,924, entitled: "Methods and Apparatus for Enhanced Power Ramping Via Multi-Threshold Detection," and filed concurrently on Dec. 2, 1998.

FIELD OF THE INVENTION

The present invention relates to methods and apparatus for requesting system access on a random access channel in a communications system and, more particularly, to methods and apparatus for providing short random access channel frames for faster access request acknowledgment in a Universal Mobile Telecommunications System.

BACKGROUND OF THE INVENTION

A major effort has been underway in the last decade to integrate multimedia capabilities into mobile communications. The International Telecommunications Union (ITU) and other organizations have been attempting to develop standards and recommendations that ensure that mobile communications of the future will be able to support multimedia applications with at least the same quality as existing fixed networks. Particularly, many global research projects have been sponsored in order to develop such next (third) generation mobile systems. Research and Development of Advanced Communication Technologies in Europe, RACE-1, and RACE-2, and Advanced Communications Technology and Services (ACTS) are examples of such efforts in Europe. It is known that in order to provide end users with the requisite service quality for multimedia communications, Internet access, video/picture transfer, high bit rate capabilities are required. Given such requirements, bearer capability targets for a third generation system have been defined as 384 kilobits per second (kb/s) for full coverage area and 2 Megabits per second (Mb/s) for local area coverage.

Universal Mobile Telecommunications System (UMTS) is a new radio access network based on 5 Megahertz Wideband Code Division Multiple Access (W-CDMA) and optimized for support of third generation services including multimedia-capable mobile communications. Since major design goals of UMTS are to provide a broadband multimedia communications system that integrates infrastructure for mobile and fixed communications and to offer, inter alia, the same range of services as provided by the fixed and wireless communications networks, UMTS must provide circuit-switched as well as packet-switched services, a variety of mixed-media traffic types, and bandwidth-on-demand. However, providing multimedia support implies the need for flexibility, that is, being able to support services with different bit rates and $E_b/N_o$ requirements, and to multiplex such services in a multiservice environment. UMTS is designed to be able to support such demands.

Referring to FIG. 1, an exemplary block diagram of a UMTS access network is shown. Particularly, a plurality of remote terminals 2 and 4 (e.g., mobile terminals) communicate with base stations (NODE-B) 6 via W-CDMA wireless links 8. The remote terminals may be a variety of devices such as a wireless phone 2 or a portable personal computer 4 with an internal or external modem. In the UMTS standard, a base station is called a NODE-B. These base stations communicate with a network component that provides radio resource management functions and is called a Radio Network Controller (RNC). Since UMTS is a W-CDMA system, soft handoffs are supported. In the case of soft handoffs, there are two base stations 6 serving one remote terminal. Thus, the remote terminal sends frames to these two base stations. When the two base stations receive the frames from the remote terminal, they send them to a Frame Selector Unit (FSU). The FSU decides which is a better frame, in terms of frame quality, to be sent to the core network. In UMTS, the FSU may be physically integrated with the RNC and as such, in FIG. 1, the RNC and FSU are shown as block 10, but also are separated functionally as block 12 (FSU) and block 14 (RNC). Other elements in the UMTS network perform conventional functions such as: the xLR databases 20, which provide home and visiting location information; and the interworking function (IWF) units. It is to be appreciated that the Universal Mobile Switching Center (UMSC) 16 serves as the mobile switching center for the base stations 6 in the UMTS. Sub-networks 18 are wireless service provider networks and CN1 through CNn are the core networks 24 to which the remote terminals are ultimately coupled.

Referring to FIG. 2, a diagram of the typical protocol stack in UMTS is shown. In UMTS, Layer 1 (L1) is the physical layer (PHY) which offers information transfer services to the MAC (Media Access Control) layer and higher layers. The physical layer transport services are described by how and with what characteristics data is transferred over the transport channels of the radio interface. Layer 2 (L2) is comprised of sublayers which include MAC, LAC (Link Access Control), and RLC and RLC' (Radio Link Control). In UMTS, the functions performed in RLC are split and thus two RLC protocols (RLC and RLC') are specified. The RLC and MAC layers provide real-time and non-real-time services. The MAC layer controls but does not carry out the multiplexing of data streams originating from different services. That is, the MAC layer, via logical channels, allows common physical communications channels (e.g., broadcast channel) to be shared by a number of remote terminals. IP (Internet Protocol) is the network layer. "Uu" refers to the UMTS-specific interface between a remote terminal and a base station, while "Iub" refers to the UMTS-specific interface between a base station and the RNC/FSU. Layer 2 of the radio access network (i.e., left side of NODE-B on the protocol stack) is split into RLC and MAC layers, while Layer 2 of the core network (i.e., right side of NODE-B on the protocol stack) is more related to the technology used to transport network layer frames, e.g., ATM (Asynchronous Transfer Mode) or Frame Relay. IP is shown as the transport protocol, however, UNMTS is not so limited. That is, UMTS can cater to other transport protocols. Further details on the protocol layers may be found in Dahlman et al., "LMTS/IMT-2000 Based on Wideband CDMA," IEEE Communications Magazine, pp. 70–80 (September 1998) and in ETSI SMG2/UMTS L2 & L3 Expert Group, "MS-UTRAN Radio Interface Protocol Architecture; Stage 2," Tdoc SMG2 UMTS-L23 172/98 (September 1998).

One of the logical channels associated with the media access control (MAC) protocol of UTMS is the random access channel (RACH). RACH is an uplink common transport channel used to carry control information and short user packets from a remote terminal. Referring to FIG. 3A, a block diagram of an exemplary hardware implementation of a non-coherent RACH detection algorithm for use in a UMTS base station (NODE-B in FIG. 1) is shown. The RACH receiver 30 is capable of providing the following functions: detection, demodulation and decoding, and acknowledgement. The purpose of detection is to determine if a RACH burst (i.e., access request signal) is being sent by a remote terminal and to resolve the strongest multipath components of the incoming burst. The receiver 30 also demodulates and decodes the message contained within the corresponding RACH to ascertain the remote terminal identifier and the requested service. After decoding a remote terminal RACH transmission, the receiver generates an acknowledgement signal which the base station transmits to the remote terminal over a Forward Access Channel (FACH).

The RACH receiver 30 preferably performs the above functions in accordance with the following structure. A RACH transmission burst is received and demodulated by mixers 32 and then filtered in filters 34. The signal is then sampled in sampling unit 36. Despreader 38 decodes the signal in accordance with the spreading sequence, in this case, 512 Gold code. The decoded signal is buffered (buffer 40) and sent to time shifting unit 50. Also, the output of the despreader 38 is provided to integrator 42. The outputs of the integrator 42 are mixed (mixer 44) and provided to timing detector 46 and then threshold detector 48. The output of the threshold detector 48 indicates whether a valid signal was received from the remote terminal. This result is provided to time shifting unit 50. If it is a valid signal (e.g., above pre-determined threshold), the decoded signal is then down-sampled by unit 52. Then, depending on the preamble, described below, the signal passes through the 16 tap filter unit 54 to the preamble signature searcher 56. The output of the searcher 56 provides the base station with the encoded remote terminal's identifier and information as to the service (s) requested by the remote terminal. The encoded information is then decoded by a convolutional decoder 58 and checked by a CRC (cyclical redundancy check) decoder 59.

Referring to FIG. 3B, a block diagram of an exemplary hardware implementation of an uplink transmitter 60 for use in a UMTS remote terminal (e.g., remote terminals 2 and 4) is shown. In a UMTS remote terminal, data modulation is dual channel QPSK (quaternary phase shift keying), that is, the I and Q channels are used as two independent BPSK (binary phase shift keying) channels. For the case of a single uplink DPDCH (dedicated physical data channel), the DPDCH and the DPCCH (dedicated physical control channel) are respectively spread by two different channelization codes ($C_C$ and $C_D$) via mixers 62 and 64 and transmitted on the I and Q branches. The I and Q branches are multiplexed in IQ MUX 66. The total spread signal I+jQ is then complex scrambled by a connection-specific complex scrambling code in mixer 68. The real portion of the signal is then filtered in root-raised cosine filter 70, while the imaginary portion of the signal is filtered in root-raised cosine filter 72. The output of filter 70 is modulated in mixer 74 with a cos($\omega t$) signal. The output of filter 72 is modulated in mixer 76 with a -sin($\omega t$) signal. The two modulated signals are then added in adder 78. The composite signal is then amplified to a predetermined signal strength (i.e., power level) in amplifier 80 and then transmitted by an antenna (not shown). A control signal from a processor associated with the remote terminal fixes the power level of the signal to be transmitted. A similar arrangement may be used in the base station.

It is known that the physical RACH is designed based on a Slotted ALOHA approach. A remote terminal can transmit a random access burst 100 at eight well-defined time offsets (Access slot #1, . . . , Access slot #i, . . . , Access slot #8) relative to the frame boundary of the received broadcast control channel (BCCH) of the current cell, as illustrated in FIG. 4A. Each access slot is offset from the previous slot by 1.25 ms. As shown in FIG. 4B, the random access burst consists of two parts, a preamble part 102 of length 1 millisecond (ms), a message part 104 of length 10 ms, and an idle time 106 of length 0.25 ms in between the preamble part and the message part. There are a total of 16 different preamble signatures that are based on the Orthogonal Gold code set of length 16 (512 Gold code). The information on the available signatures and time offsets are broadcast on BCCH. Based on this structure, if the receiver has 128 (16 preamble signatures multiplied by 8 timeslots) parallel processing units, 128 random access attempts can be simultaneously detected. In other words, we have equivalent 128 random access channels for a maximum configured base station for the current cell. This arrangement is as per the current Layer 1 Expert Group specification in UTRAN/FDD Physical Layer Description Document, "SMG2 UMTS Physical Layer Description FDD Part," Tdoc SMG2 UMTS-L1 221/98.

Referring to FIG. 4C, the existing RACH access slot structure is shown in which the frame structure (Frame 0, Frame 1, . . . , Frame n) is based on 10 milliseconds (ms). Also, it is assumed that the receiver requires a minimum of 2.5 ms to process an access burst. As shown, those remote terminals that have selected time offsets 0, 1, 2, 3, 4, and 5, can receive their MAC acknowledgements (from the base station) within 8.75 ms of their transmissions. That is, the maximum waiting period for an access burst (request signal), transmitted by a remote terminal within slots 0 through 5, is 8.75 ms. For example, Burst 0 is transmitted by a remote terminal at the start of Frame 0 and the remote terminal may receive an acknowledgement in response at the start of Frame 2, i.e., 8.75 ms later. Bursts 1 through 5 receive acknowledgements progressively sooner, up to Burst 5 which can receive an acknowledgement 2.5 ms after transmission. Acknowledgements generated by a base station for transmission in a given frame are typically grouped together in a common packet broadcast to the transmitting remote terminals.

However, as is evident, those terminals that have selected time offsets 6 and 7 can only receive their MAC layer acknowledgements within a maximum of 11.25 ms of their transmission, i.e., Burst 6 at 11.25 ms and Burst 7 at 10 ms. Again, this has to do with the fact that the minimum time to process an access request is assumed to be 2.5 ms. As such, access bursts 6 or 7 transmitted by remote terminals in Frame 1 extend beyond the 2.5 ms minimum processing period such that the base station cannot process the request and transmit acknowledgements in Frame 2. Thus, such remote terminals do not receive respective acknowledgements until Frame 3.

SUMMARY OF THE INVENTION

The present invention provides an improved RACH access burst arrangement and frame structure. That is, the invention provides methods and apparatus for supporting more than one access burst length in the UMTS access channel structure. Preferably, two access burst lengths are supported, e.g., 5 ms and 10 ms. Such an arrangement is advantageous in applications where it is beneficial to have fast access latency such as, for example, voice or other forms of real-time traffic. Also, the invention provides methods and apparatus for supporting multiple frame sizes. It is to be appreciated that further enhancement to access latency can be obtained by having the UMTS physical layer support multiple frame sizes. It is to be appreciated that the access burst signal transmitted by a remote terminal over the RACH may be an access request or data packets in the case where the RACH is being utilized for UMTS short message services.

In one aspect of the invention, apparatus for improving access latency in a random access channel in a communications system including at least one base station, comprises a remote terminal configured for selecting a time duration associated with an access signal (e.g., access request or data packets), the time duration being selected from among time durations which range from being substantially equivalent to a length of a transmission frame of the base station to being less than the length of the transmission frame. Preferably, the remote terminal may choose between an access burst duration with a message portion of about 10 ms and about 5 ms. The remote terminal then transmits the access signal having the selected time duration associated therewith to the base station over the random access channel in a selected time offset slot associated with the channel. Alternatively, the remote terminal may indicate to the base station, in advance of the access burst, the time duration it has selected.

In another aspect of the invention, apparatus for improving access latency in a random access channel in a communications system including at least one remote terminal, comprises a base station configured for selecting a transmission frame time duration associated with a random access channel, the transmission frame time duration being selected from among one or more supported time durations. Preferably, the base station may choose between a frame size of about 10 ms and about 5 ms. The base station is also configured for acknowledging a successful access signal transmitted by the remote terminal over the random access channel in a selected time offset slot associated with the channel. Alternatively, the base station may indicate to the remote terminal, in advance, the transmission frame time duration it has selected.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 4C illustrates the existing access slot structure used in a UMTS RACH;

DETAILED DESCRIPTION OF PREFERRED EMBODIMENTS

The present invention is described below in the context of the MAC layer of the UMTS, particularly, with respect to detection of a random access request signal in the random access channel or RACH. However, it is to be appreciated that the teachings of the invention discussed herein are not so limited. That is, the access methodologies of the invention are applicable to other communications systems where remote terminals (e.g., mobile or fixed) transmit and receive signals (e.g., data and control signals) to and from a base station or other communications system access point. Also, as mentioned, the access signal need not necessarily be an access request. That is, in the case of UNMTS short message services, short data packets are transmitted over the RACH as access burst signals. Further, it is to be understood that methodologies described herein for use in a remote terminal or a base station are executed by one or more processors respectively associated therewith. The term "processor" as used herein is intended to include any processing device, including a CPU (central processing unit), or microprocessor, and associated memory. The term "memory" as used herein is intended to include memory associated with a processor or CPU, such as RAM, ROM, a fixed memory device (e.g., hard drive), or a removable memory device (e.g., diskette). In addition, the processing unit may include one or more input devices, e.g., keypad or keyboard, for inputting data to the processing unit, as well as one or more output devices, e.g., CRT display, for providing results associated with the processing unit. Accordingly, software instructions or code associated with implementing the methodologies of the present invention may be stored in associated memory and, when ready to be utilized, retrieved and executed by an appropriate CPU. Also, the term "remote terminal" refers to any device capable of communications with a base station. For example, a remote terminal may be mobile (e.g., wireless phone or portable personal computer with a wireless modem) or fixed (e.g., fixed personal computer with a wireless modem). Also, the terms "base station" and "node__b," are used interchangeably herein.

Figure 1:
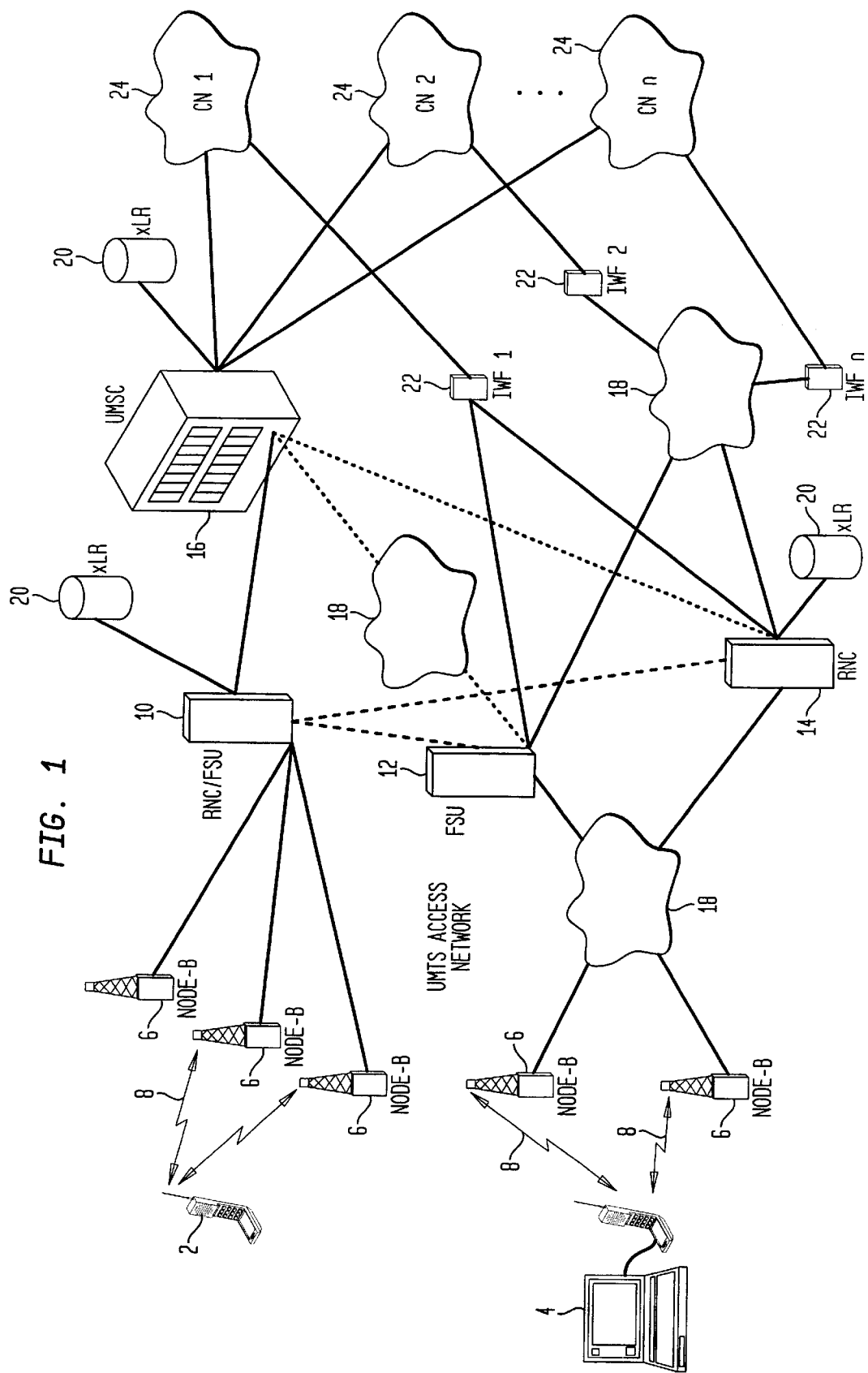
FIG. 1 is a block diagram of a UMTS access network.
Figure 2:
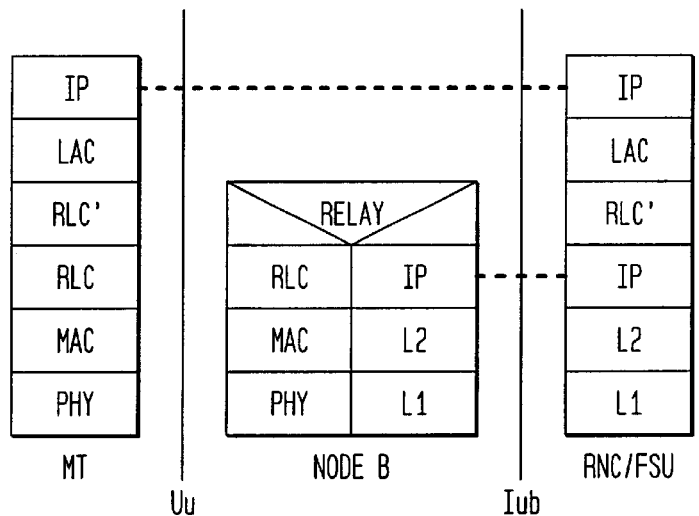
FIG. 2 is a diagram of a protocol stack associated with a UMTS.

Referring back to FIG. 1 and as previously mentioned, it is to be understood that the remote terminals, 2 and 4, are coupled to the UMTS access network through a wireless interface with base stations 6. In order to establish communications, the remote terminals send and receive media access control (MAC) frames over the wireless interface to and from the base stations 6. In the case of the terminal 4, an internal or external modem may be used to provide a wireless connection with the base stations. A remote terminal, such as remote terminal 2, typically has its own internal modem. Nonetheless, packets are typically generated or received at the remote terminal on a bursty random basis. The packets are buffered at the remote terminals until they are transmitted uplink to a base station. The base stations 6, as is known, provide wide-area wireless coverage and multiplex remote terminal traffic from their respective coverage area to their system's mobile switching center, e.g., UMSC 16 in FIG. 1. The base stations also broadcast (downlink) packets that are destined for one or more of the remote terminals in its cell.

The UMTS multiple access scheme is a time-slotted system (i.e., Slotted ALOHA approach) in which a random access channel (RACH) and a packet transmission channel are formed on a slot-by-slot basis. Time slot duration in each channel is chosen based on the particular system implemented. Generally, remote terminals that have packets to send transmit access requests via the RACH to a base station.

Figure 3B:
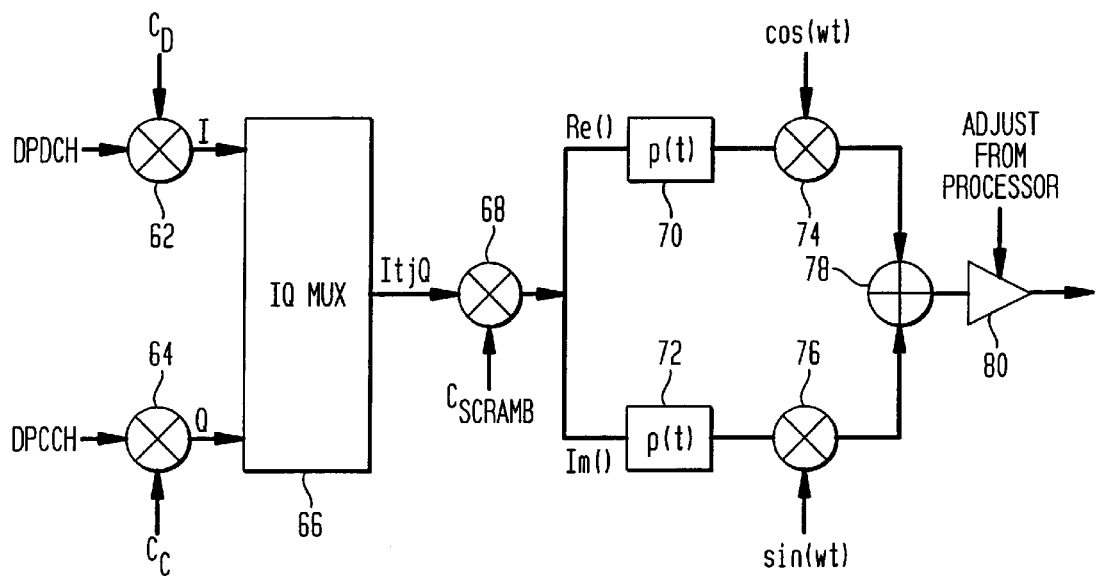
FIG. 3B is a block diagram of a transmitter for use in a UMTS.
Figure 5A:
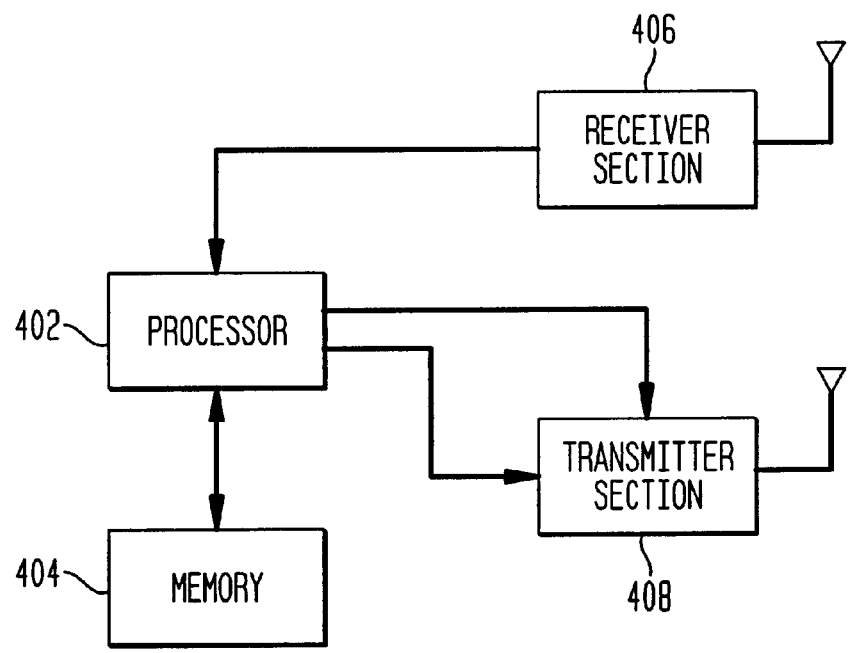
FIG. 5A is a block diagram of a remote terminal for use according to the present invention.

Referring to FIG. 5A, a block diagram of a remote terminal (e.g., remote terminal 2 and 4) for use according to the present invention is shown. The remote terminal includes a processor 402 for controlling operations associated with the terminal, in cooperation with its associated memory 404, including the methodologies of the invention to be described in detail below. The remote terminal also includes a receiver section 406 and a transmitter section 408. The specific elements of the receiver section 406 are not critical to the invention and, as such, are not described in detail herein. That is, a conventional receiver section capable of demodulating and decoding W-CDMA type signals may be employed. The transmitter section 408 may also be of a conventional type capable of encoding and modulating W-CDMA type signals. The transmitter section may be as shown in FIG. 3B. Specifically, the processor 402 generates an access request signal to be transmitted by the transmitter section 408 to the base station within a particular time slot (time offset) in the RACH. The receiver section 406 receives the acknowledgement signal from the base station and provides it to the processor 402.

Figure 3A:
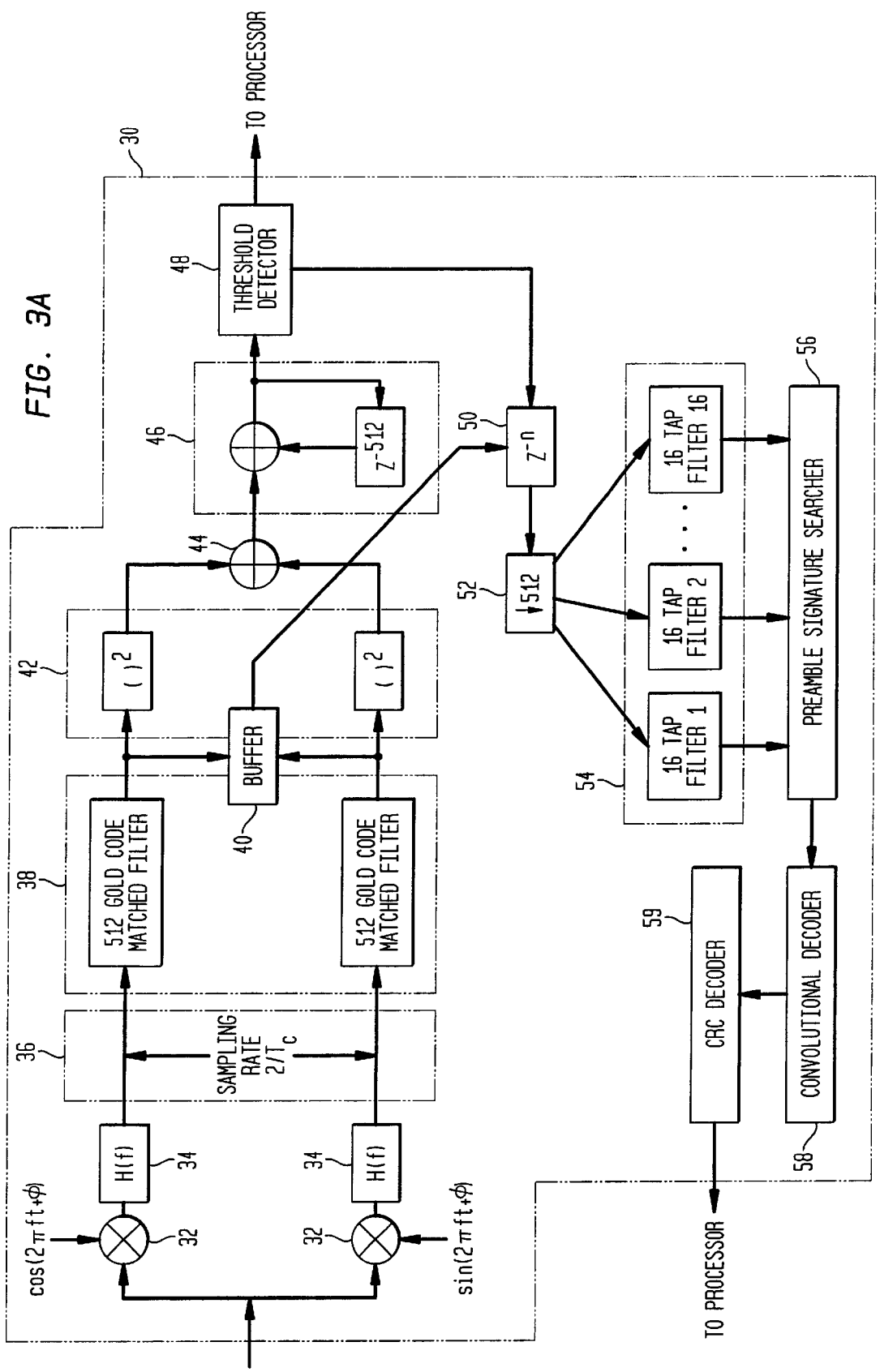
FIG. 3A is a block diagram of a non-coherent RACH receiver for use in a UMTS.
Figure 5B:
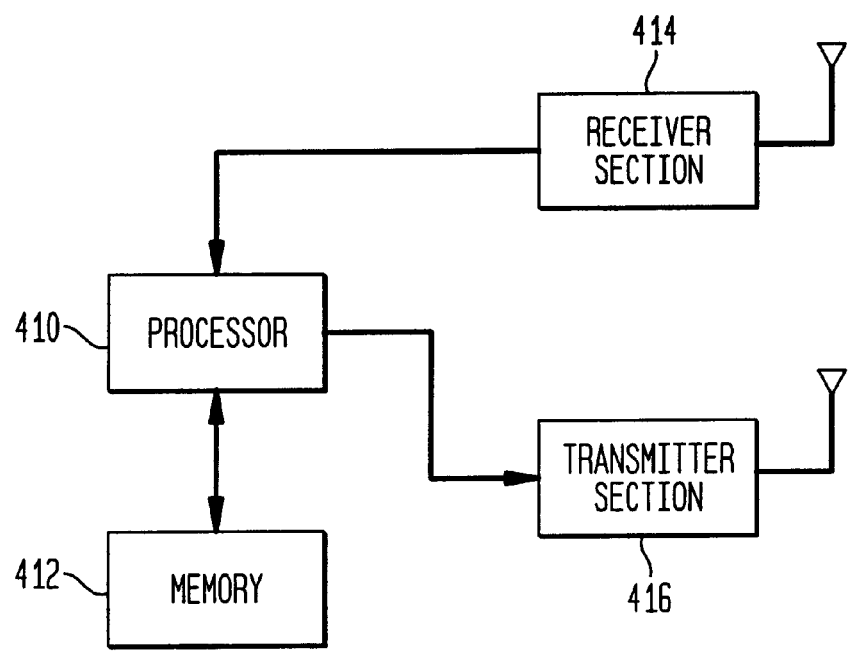
FIG. 5B is a block diagram of a base station for use according to the present invention.

Referring to FIG. 5B, a block diagram of a base station (e.g., base station 6) for use according to the present invention is shown. The base station includes a processor 410 for controlling operations associated with the station, in cooperation with its associated memory 412, including the methodologies of the invention to be described in detail below. The base station also includes a receiver section 414 and a transmitter section 416. The specific elements of the transmitter section 416 are not critical to the invention and, as such, are not described in detail herein. That is, a conventional transmitter receiver section capable of encoding and modulating W-CDMA type signals may be employed. The transmitter section may be similar to that shown in FIG. 3C. The receiver section 414 may also be of a conventional type capable of demodulating and decoding W-CDMA type signals. For example, the receiver section 414 may be a RACH receiver as shown in FIG. 3A. Accordingly, after the receiver section 414 receives an access request signal and provides it to the processor 410, the processor generates a MAC acknowledgement signal which is then transmitted by the transmitter section 416.

As mentioned and as will be further explained, the present invention provides improved access latency in UMTS RACH by providing for shorter access burst lengths as compared to the conventional access burst length. Also, additional latency improvement is realized in accordance with the invention by supporting multiple frame sizes rather than only a single frame size as in the conventional UMTS RACH, as will be explained. It is to be understood that such fast detection methodologies and apparatus provide improved throughput in the UMTS since access requests and acknowledgements are exchanged faster than in the conventional UMTS approach.

Figure 4A:
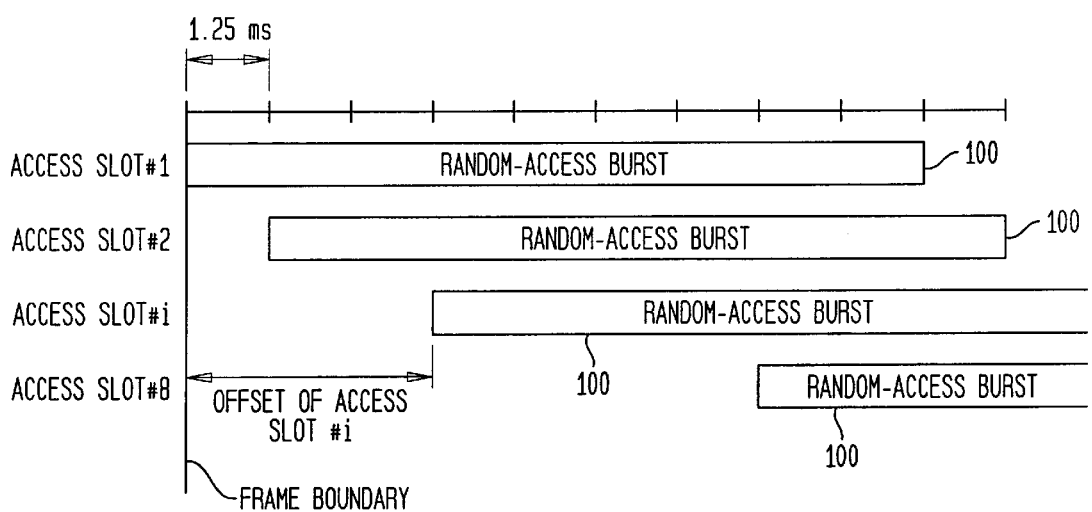
FIGS. 4A and 4B illustrate access slots and a structure of a random access burst used in a UMTS RACH.
Figure 4B:
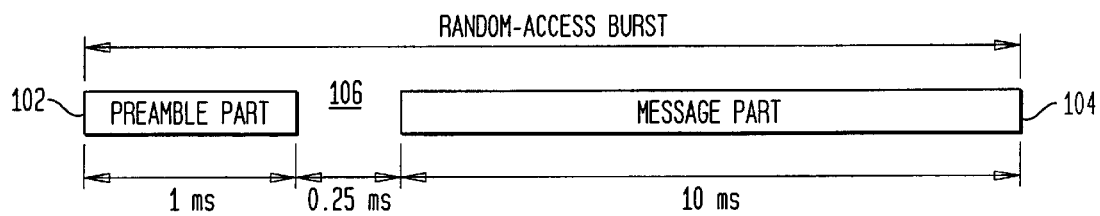
Figure 6:
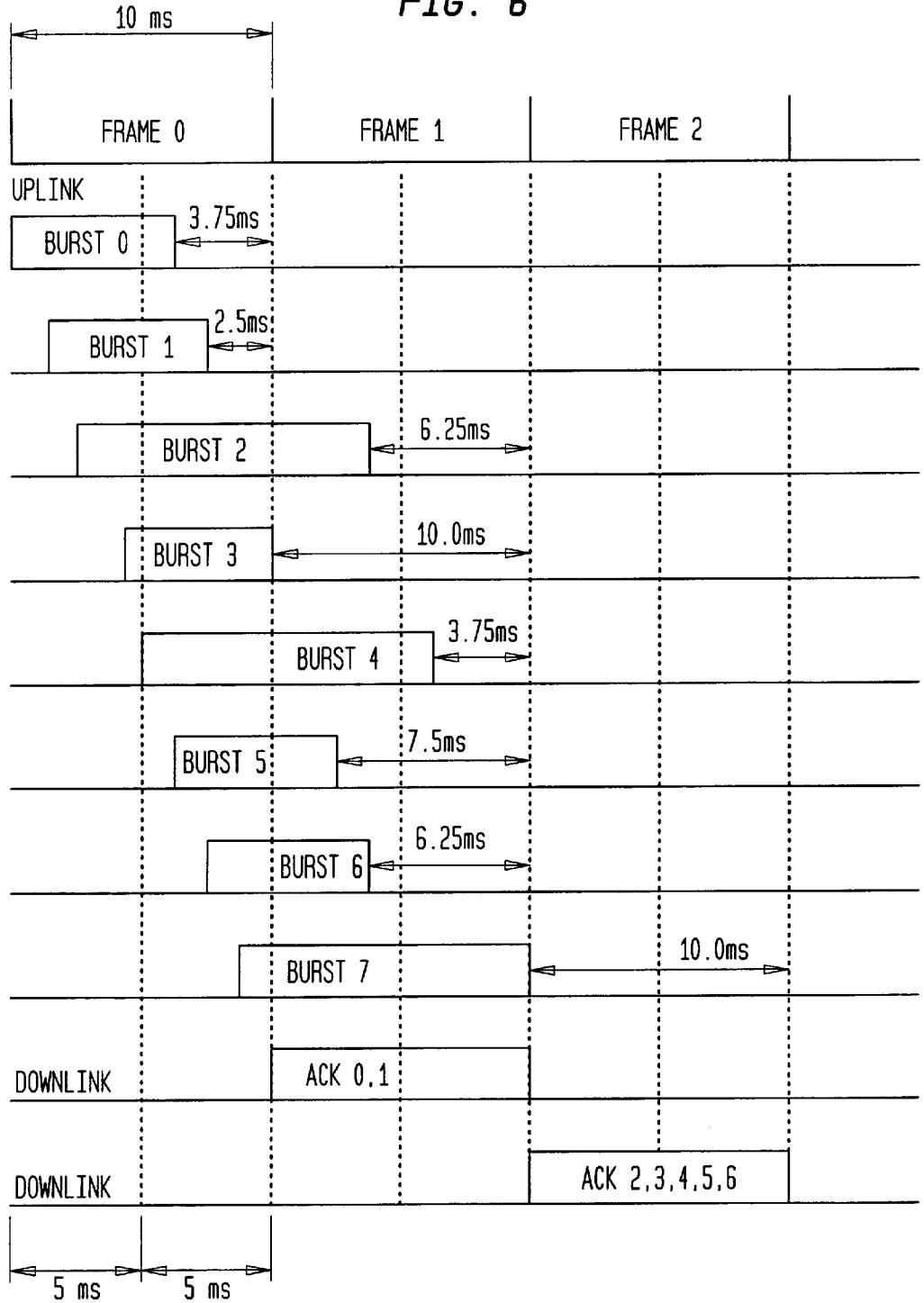
FIG. 6 illustrates an exemplary access slot structure for use in a UMTS RACH according to an embodiment of the invention.

Referring now to FIG. 6, an exemplary access slot structure for use in a UMTS RACH according to an embodiment of the invention is shown. In this embodiment, the remote terminals transmit access request bursts that are either 5 ms (short burst) or 10 ms (normal burst) in length. That is, the message part 104 (FIG. 4B) of the access burst is either 5 ms or 10 ms, however, the preamble part (1 ms) and the idle part (0.25 ms) remain the same. Therefore, the complete access burst length is either 6.25 ms or 11.25 ms. It is to be understood that, in one embodiment, the remote terminal informs the base station in advance which burst duration it intends to transmit. This may be done on the uplink control channel formed between the remote terminals and a base station. Alternatively, the remote terminal may dynamically select the burst duration, that is, without expressly informing the base station. In such case, the base station processes the burst as if it is a 5 ms burst and, if appropriate portions of the message are not part of the first 5 ms, then the base station processes the next 5 ms, as it is likely that the access burst is a normal burst length (10 ms). In FIG. 6, Bursts 0, 1, 3, 5, and 6 are short bursts and Bursts 2, 4, and 7 are normal bursts. The frame size remains 10 ms. The dashed lines indicate 5 ms intervals within each frame of 10 ms. Cases where the access request is successful (i.e., detected and decoded by the base station and an acknowledgement signal generated by the base station and received by the remote terminal) are shown. It is also assumed that the receiver at the base station requires a minimum of 2.5 ms to process an access burst. As can be seen, for example, with respect to Bursts 0 and 1, since they are short bursts starting in Frame 0, an acknowledgement signal may be received within a maximum of 3.75 ms, that is, in Frame 1. In other words, with respect to Bursts 0 and 1, since 2.5 ms (Burst 1) or more (3.75 ms for Burst 0) are left between the end of each burst and the end of Frame 0, the request can be processed by the base station so that acknowledgements can be sent in Frame 1. Again, acknowledgements generated and then transmitted in a given frame are preferably grouped together in a common packet transmitted to the sending remote terminals.

As can be seen, if an access burst does not end with at least 2.5 ms remaining in the particular frame in which it ends, an acknowledgement must wait until the second following frame. For example, Burst 3 ends just at the end of Frame 0, so an acknowledgement must wait until Frame 2. However, it is to be appreciated that the use of short and normal burst lengths can achieve improved access latency, i.e., fast acknowledgement, with respect to individual remote terminals, as well as in the system as a whole.

Figure 7:
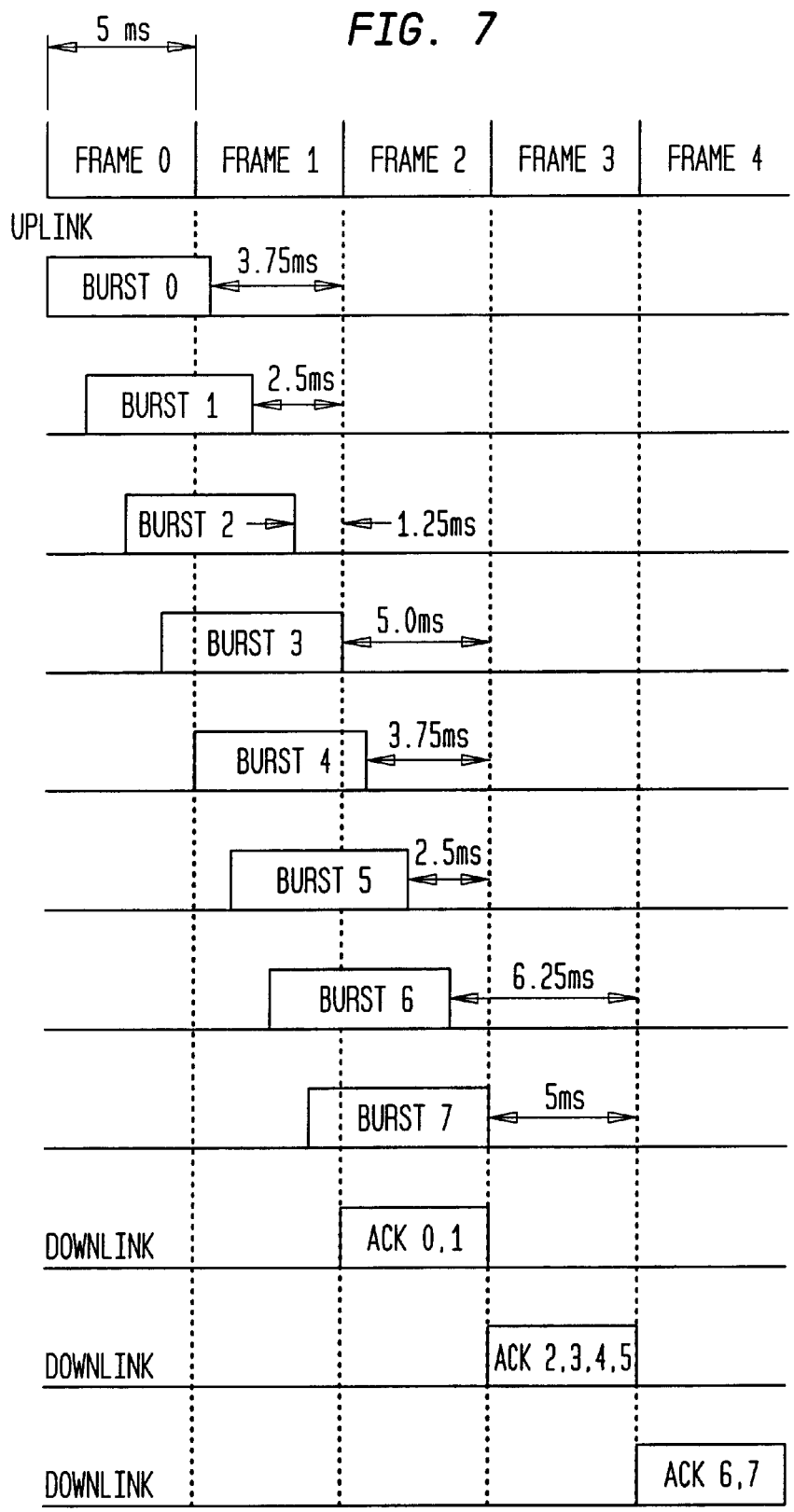
FIG. 7 illustrates an exemplary frame size structure for use in a UMTS RACH according to another embodiment of the invention.
Figure 8:
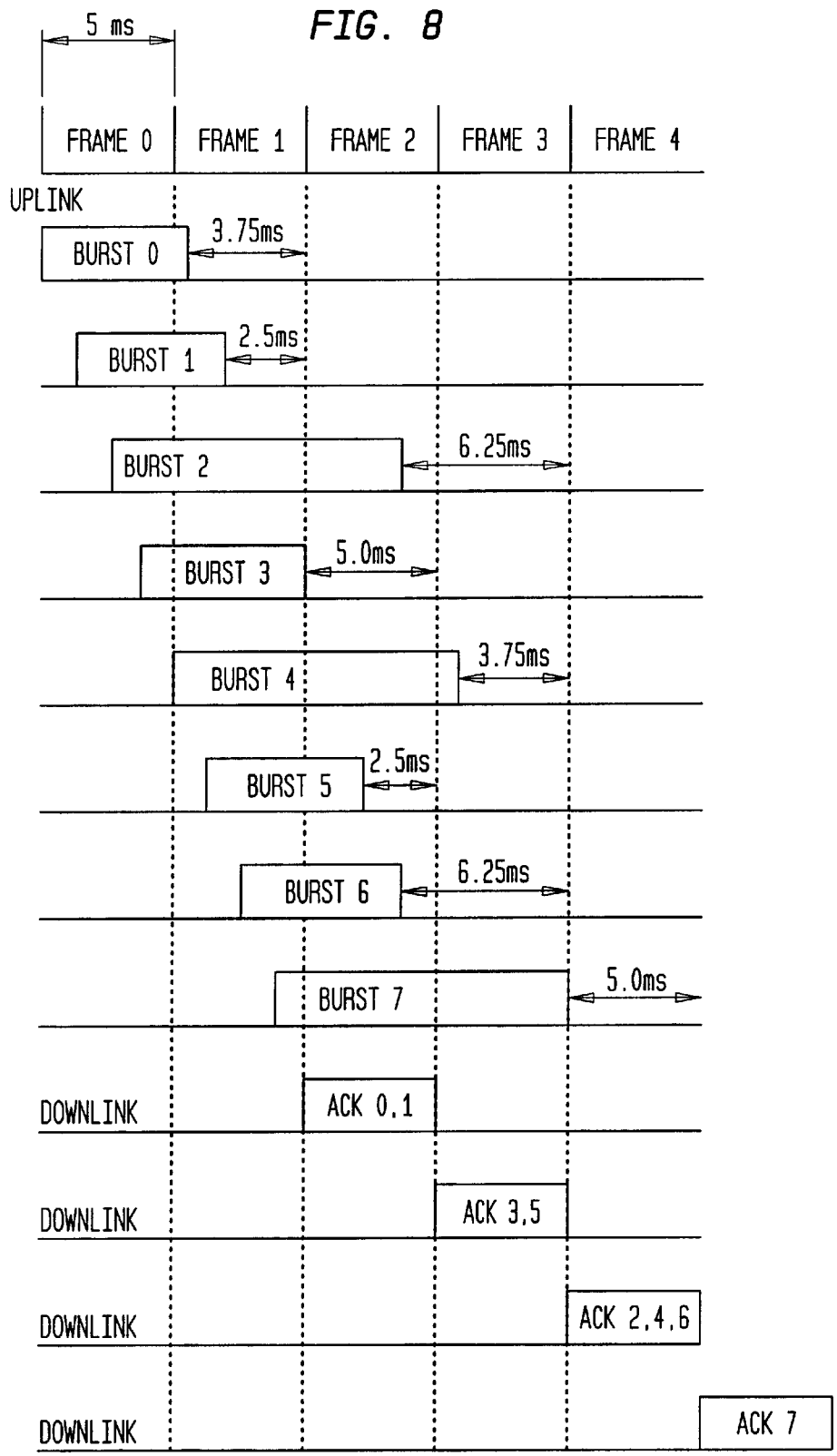
FIG. 8 illustrates an exemplary frame size structure for use in a UMTS RACH according to yet another embodiment of the invention.

In accordance with another aspect of the invention, a further enhancement to the access latency can be obtained by requiring the UMTS physical layer to support multiple frame sizes. This may preferably be accomplished by having a base station indicate to the terminals which frame size it is currently employing via a message transmitted over a downlink broadcast control channel (BCCH). Preferably, two different frame sizes may be supported, e.g., 5 ms (short frame size) and 10 ms (normal frame size). Referring now to FIGS. 7 and 8, examples of frame size structures of the invention are shown. In FIG. 7, the case where 5 ms frames with short access bursts are used is shown. With the 5 ms frame structure and short access bursts, those terminals which have chosen time offset 0 through 5 are able to receive their MAC layer acknowledgements within 3.75 ms after their transmissions. Those which choose time offsets 6 and 7 are able to receive their acknowledgements within 6.25 ms after their transmissions. Again, the latency shown for acknowledgement delay is for successful bursts. FIG. 8 shows the case where a mixture of 5 ms (short) and 10 ms (normal) access bursts and 5 ms frames are employed. In this case, the worst case delay for receiving any MAC layer acknowledgement is 6.25 ms after transmission.

Alternatively, similar to the remote terminal dynamically changing its access burst length, the base station may dynamically select a different frame size without broadcasting such change to the remote terminals. In such case, the remote terminal processes a frame as if it is a 5 ms frame and, if appropriate portions of the acknowledgement are not part of the first 5 ms, then the remote terminal processes the next 5 ms, as it is likely that the base station is operating with a 10 ms frame structure.

Figure 9A:
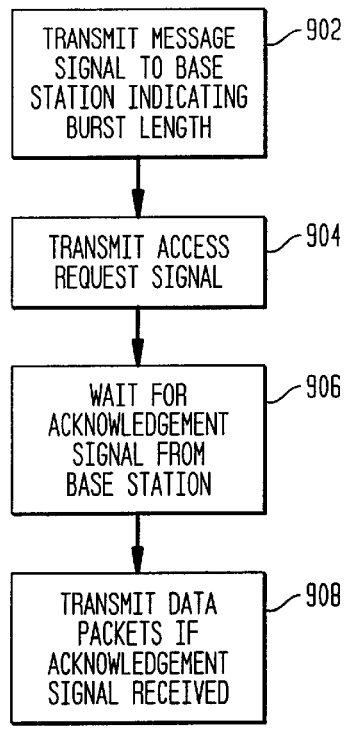
FIG. 9A is a flow chart of an access request method for use in a remote terminal according to an embodiment of the invention.

Referring now to FIG. 9A, a flow chart of an access request method for use in a remote terminal according to an embodiment of the invention is shown. In step 902, a remote terminal transmits a signal to a base station over an uplink control channel indicating the selected length of the access burst it will transmit. For example, as in the embodiments above, the remote terminal may indicate that it will transmit a short burst (5 ms message duration) or a normal burst (10 ms message duration). Of course, in the case of a dynamic selection of access burst length, the remote terminal does not need to expressly inform the base station. The remote terminal then transmits its access request signal, having the duration previously indicated to the base station, over the RACH (step 904). The remote terminal then waits for acknowledgement from the base station indicating a successful request (step 906). After receiving a successful acknowledgement, the remote terminal then transmits its desired data packets (step 908). In the case of where the access burst transmitted in step 904 includes data packets associated with UMTS short message services, step 908 is not necessary.

Figure 9B:
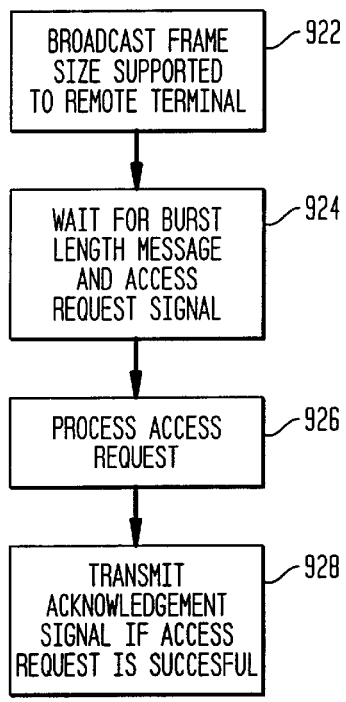
FIG. 9B is a flow chart of an access request method for use in a base station according to an embodiment of the invention.

Referring now to FIG. 9B, a flow chart of an access request method for use in a base station according to an embodiment of the invention is shown. In step 922, the base station broadcasts the selected frame size it will support. For example, as in the embodiments above, the base station may indicate that it will support 5 ms or 10 ms frames. Of course, in the case of a dynamic selection of frame size, the base station does not need to expressly inform the remote terminal. Then the base station waits for access request signals (step 924) and processes signals received (step 926). If a proper access request is received, the base station transmits an acknowledgement signal to the sending remote terminal indicating that the terminal may now transmit data packets (step 928).

Figure 10:
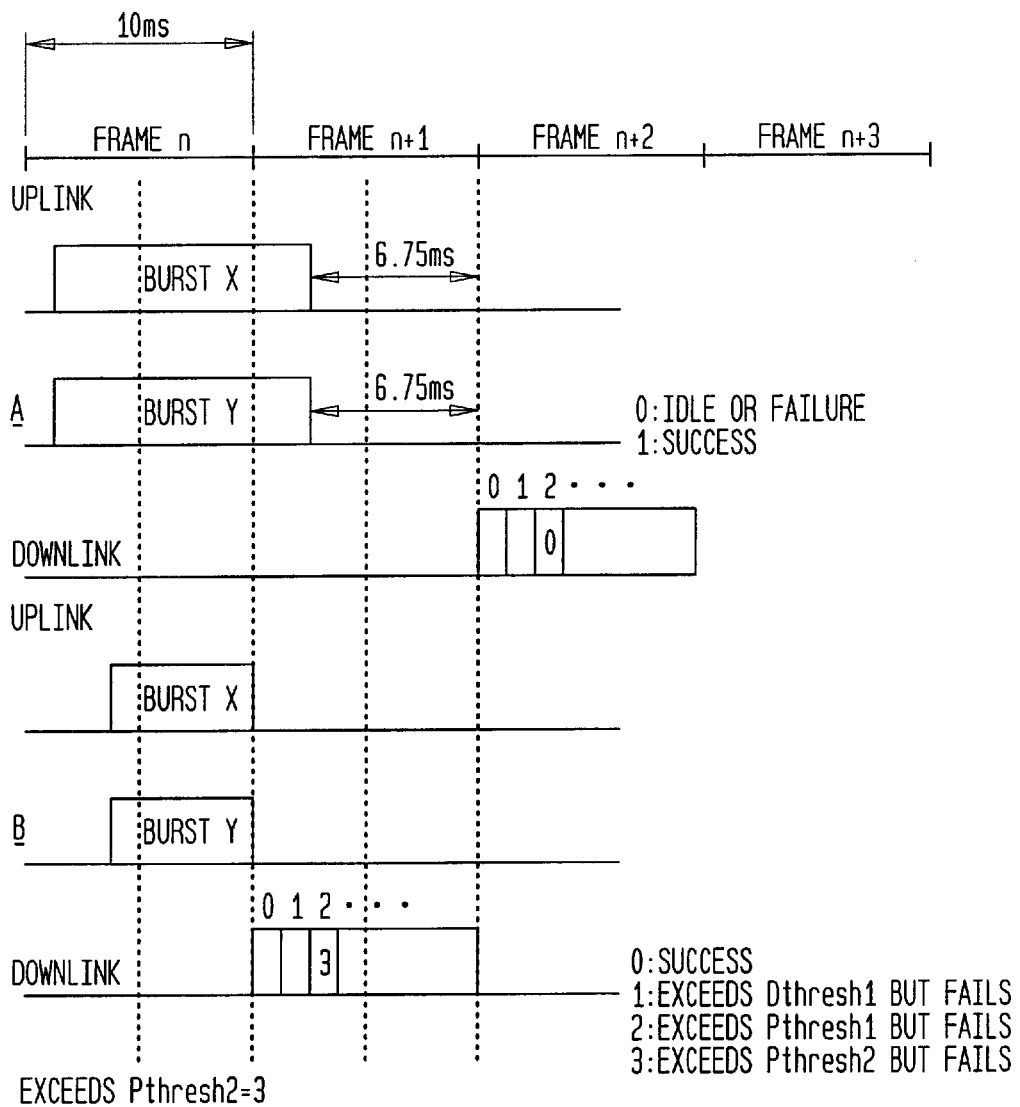
FIG. 10 illustrates an exemplary comparison between an access slot structure according to an embodiment of the invention implementing a multi-threshold detection method and the existing access slot structure used in a UMTS RACH.

Referring now to FIG. 10, an exemplary comparison between an access slot structure (denoted as B) according to an embodiment of the invention implementing a multi-threshold detection algorithm, described below, and the existing access slot structure (denoted as A) used in a UMTS RACH is shown. It is to be appreciated that implementing the fast detection algorithm of the invention with the multi-threshold detection algorithm results in an even shorter time period for determining whether an access request signal is successfully received. One reason an access request signal may not be successfully received using a conventional RACH receiver is if the access request signal (denoted as X) was sent in the same time offset slot as an access request signal (denoted as Y) sent by another remote terminal. In such a case, the bursts may arrive sufficiently far apart for one of the signals to be captured but not decoded correctly due to weak signal strength. In such a case, a conventional RACH receiver with a single detection threshold may not detect one or both signals (X and Y) since they fall below the single detection threshold. This situation is illustrated in FIG. 10 with respect to a conventional arrangement (A) and the inventive arrangement (B), wherein in both cases bursts X and Y are transmitted in access time offset 2. Before explaining the advantages of such inventive arrangement, the multi-threshold detection algorithm will be explained below.

Multi-threshold Detection Algorithm

The following is a description of a multi-threshold detection method for use in accordance with a RACH receiver of a base station and a transmitter of a remote terminal. This algorithm is described in a patent application entitled: "Methods And Apparatus For Enhanced Power Ramping Via Multi-threshold Detection," filed concurrently herewith.

Figure 11:
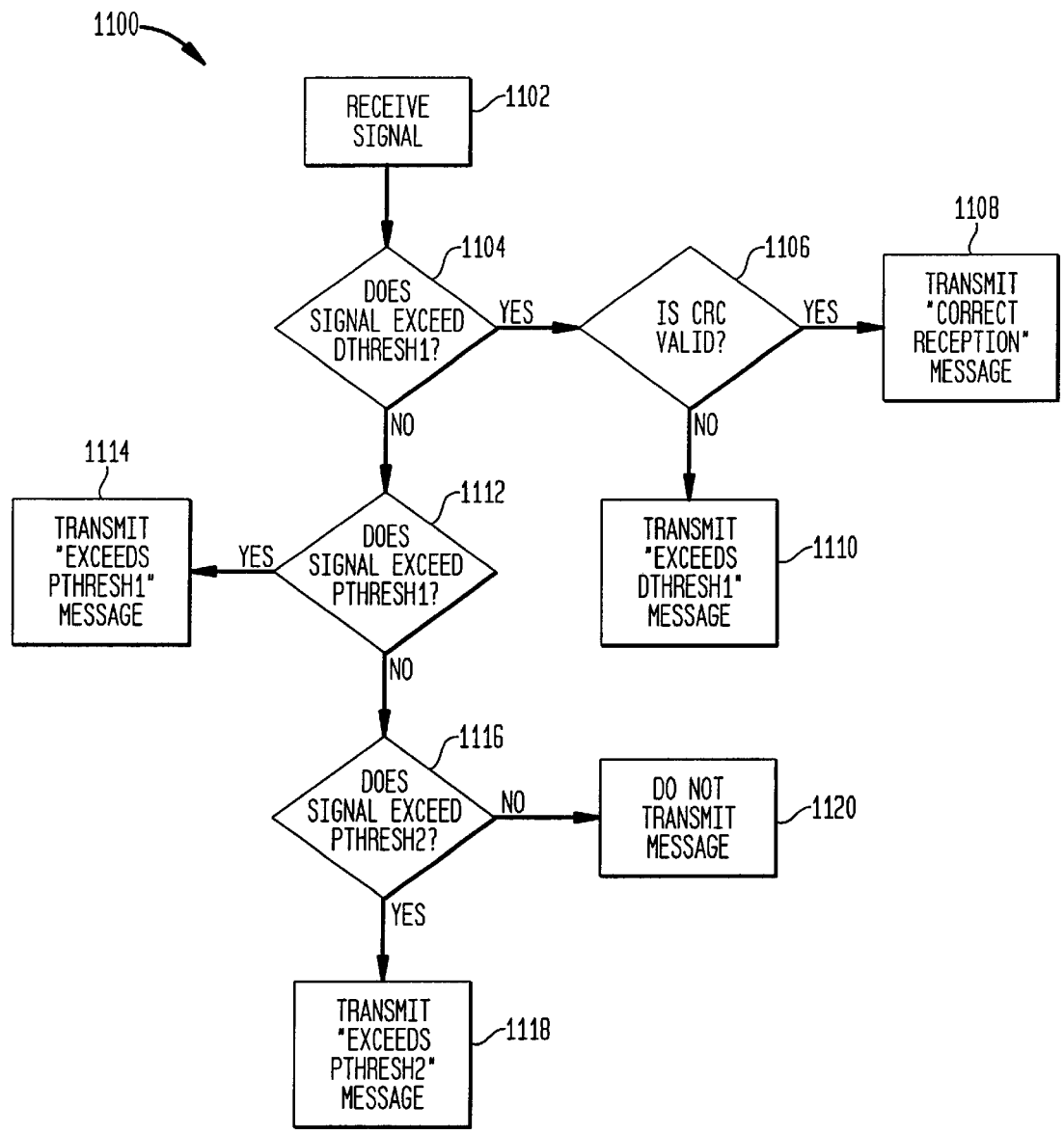
FIG. 11 is a flow chart of a multi-threshold detection method implemented in a base station.
Figure 13:
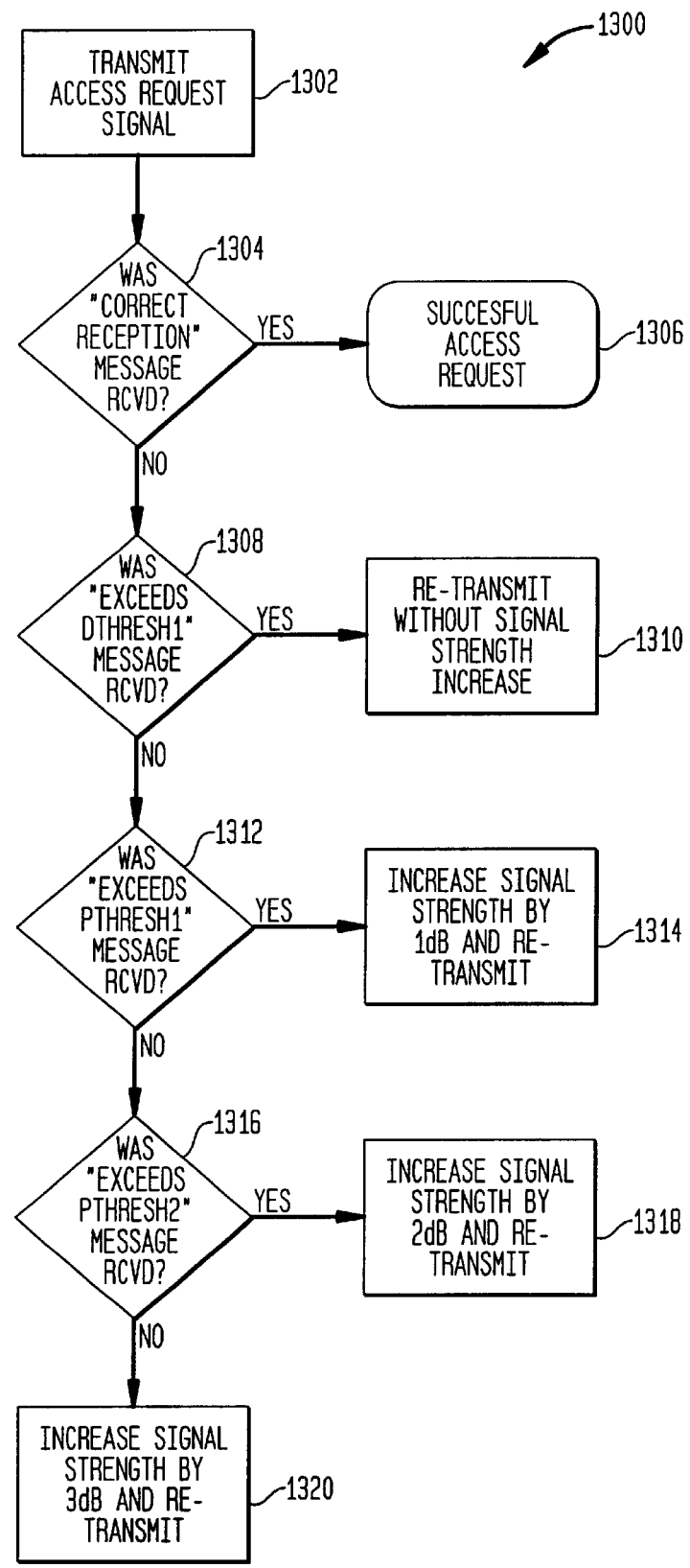
FIG. 13 is a flow chart of a multi-threshold detection method implemented in a remote terminal.

Referring now to FIGS. 11 and 13, flow charts of a multi-threshold detection method are shown. The steps of FIG. 11 (1102 through 1120) are performed in a base station and the steps of FIG. 13 (1302 through 1320) are performed in a remote terminal. First, in step 1102, the base station receives a signal, presumably a request signal transmitted (step 1302) by a remote terminal seeking access to the communications system via the base station. Next, in step 1104, the base station determines whether the signal exceeds DTHRESH1 (detection threshold level). DTHRESH1 may be, for example, about 7 dB. This determination may be accomplished by, for example, the threshold detector 48 (FIG. 3A), which then informs the processor 410 (FIG. 5B). Then, in step 1106, the base station determines whether the CRC is valid. This determination may be accomplished by, for example, the CRC decoder 59 (FIG. 3A), which also then informs the processor 410 (FIG. 5B).

If the signal exceeds DTHRESH1 and the CRC is found to be valid, the base station generates (via processor 410) and transmits (through its transmitter section 416) a "correct reception" message to the remote terminal (step 1108). If the remote terminal receives the "correct reception" message (via its receiver section 406), in step 1304, it knows that its access request was successful (step 1306) and it can then proceed to transmit desired data to the base station.

However, returning to the base station, if the CRC is not valid, the base station transmits, in step 1110, an "exceeds DTHRESH1" message to indicate that the access request signal was of sufficient power, but that the CRC was not valid. If this message is received by the remote terminal (step 1308), the remote terminal re-transmits the request signal without increasing the power level of the signal (step 1310).

It is to be appreciated that while this description explains what happens when an original access request signal is sent and received with respect to the remote terminal and the base station, each time the base station receives a signal (re-transmitted or original signal), the detection algorithm returns to step 1102 to repeat the detection process.

Returning now to step 1104 in the base station, if the original signal transmitted by the remote terminal did not exceed DTHRESH1, the base station (threshold detector)

determines whether the signal exceeds PTHRESH1 (step 1112). It is to be understood that PTHRESH1 (power threshold level 1) is preferably about 5 dB. If the signal strength of the originally received signal exceeds PTHRESH1, then the base station transmits an "exceeds PTHRESH1" message to the remote terminal (step 1114). When the remote terminal receives this message (step 1312), the remote terminal increases its signal strength by about 1 dB and re-transmits the access request signal (step 1314). It is to be understood that the remote terminal increases the signal strength by the processor 402 receiving the message from its receiver section 406 and sending a control signal to its transmitter section 408, particularly, the output amplifier 80, to increase the power level of the signal to be transmitted.

Returning to step 1112 in the base station, if the original signal transmitted by the remote terminal did not exceed PTHRESH1, the base station (threshold detector) determines whether the signal exceeds PTHRESH2 (step 1116). It is to be understood that PTHRESH2 (power threshold level 2) is preferably about 3 dB. If the signal strength of the originally received signal exceeds PTHRESH2, then the base station transmits an "exceeds PTHRESH1" message to the remote terminal (step 1118). When the remote terminal receives this message (step 1316), it increases its signal strength by about 2 dB and re-transmits the access request signal (step 1318).

However, if the original signal does not exceed PTHRESH2, then the base station does not transmit any message (step 1120). Since no message is received by the remote terminal after transmitting the original signal, the remote terminal increases its signal strength by about 3 dB and re-transmits the access request (step 1320).

Figure 12A:
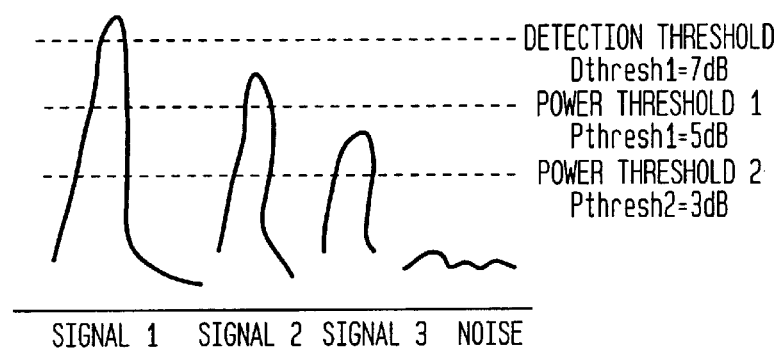
FIGS. 12A and 12B are graphical representations illustrating the multi-threshold detection method of FIG. 11.
Figure 12B:
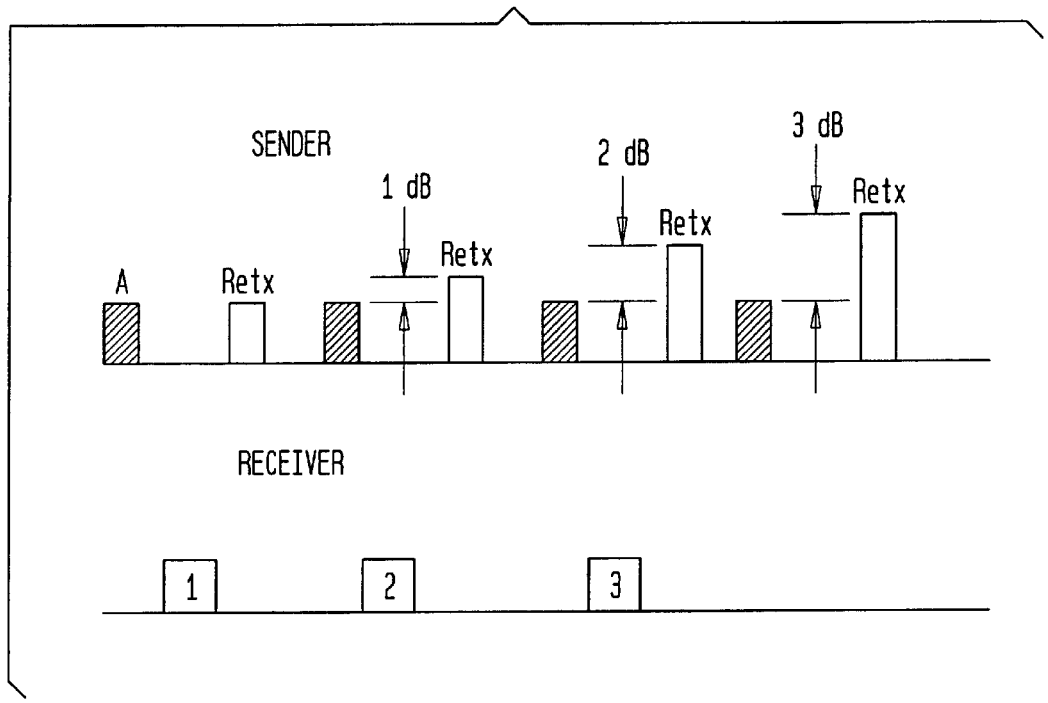

Referring to FIG. 12A, a graphical representation of the detection thresholds (DTHRESH1, PTHRESH1, PTHRESH2) is shown. It is to be appreciated that more or less threshold levels may be included so that finer or coarser detection may accomplished, respectively. Also, other thresholds may be employed, for example, rather than a signal having to exceed the threshold value, the signal being equal to the threshold may be used to trigger transmission of the above-described messages. Advantageously, access request signals below a typical detection level are still detected by a receiver, implementing the multi-threshold detection method, so that these weaker signals are distinguished from collision-effected signals or noise. Thus, while only signal 1 would be detected using an existing detection algorithm, signals 1, 2, and 3 are detected by detection algorithm. Lastly, FIG. 12B is a graphical representation illustrating the transfer of messages between the sender (remote terminal) and receiver (base station) as explained above in the context of FIGS. 11 and 13. The messages 1, 2, and 3 correspond to the messages "exceeds DTHRESH1," "exceeds PTHRESH1," and "exceeds PTHRESH2" transmitted by the receiver. The first shaded (hatched) message, labeled A, is the original signal transmitted by the sender. Each re-transmitted signal (retx) thereafter corresponds to the signal sent in response to a base station message. The magnitude of each re-transmitted signal is shown proportional to the increase in signal strength. The magnitude of the original signal (shaded or hatched) is shown along side the re-transmitted signal for comparison. It is to be appreciated that other power increments may be employed.

Returning now to FIG. 10, it can be seen that in the case where the existing RACH procedure is used (denoted as A), each remote terminal beginning an access burst in Frame n, must wait until Frame n+2 before discovering their access request transmission failed. As shown, a value of zero (0) in the 2nd acknowledgement field (corresponding to time offset 2) of the acknowledgement message received during the downlink indicates to each remote terminal that its access burst was not successfully received, i.e., failed. It is to be understood that an access burst signal may fail for several reasons. One typical reason is that two remote terminals attempted to transmit access bursts in the same time slot (offset) and the bursts collided, as is the case in example A in FIG. 10. On the other hand, a value of one (1) in the corresponding field of the acknowledgement message received during the downlink indicates to a remote terminal that its access burst was successfully received, i.e., succeeded. Thus, the remote terminals in example A do not know that their respective access bursts failed until some time in Frame n+3. This is because an acknowledgement indicator from a base station can only be processed after the entire downlink frame is received.

However, using the detection algorithm of the invention, the acknowledgement delay is advantageously smaller for unsuccessful bursts. As shown, if bursts X and Y, which are of the short burst length type, are transmitted in the same time offset slot (e.g., time offset slot 2) and collide resulting in signal strengths below 5 dB but above 3 dB, each remote terminal receives an "exceeds PTHRESH2" message and increase its signal strength accordingly for re-transmission. The acknowledgement signal in example B shows a value of three (3) in the 2nd acknowledgement field (corresponding to time offset 2), indicating that the received signal exceeded PTHRESH2 but still failed to be decoded. On the other hand, a value of 0 indicates a successful access burst, a value of 1 indicates that the received signal exceeded DTHRESH1 but still failed, and a value of 2 indicates that the received signal exceeded PTHRESH1 but still failed. Since the message is sent in the next succeeding frame (Frame n+1), a remote terminal could re-transmit before the end of that frame or in the next frame.

Although illustrative embodiments of the present invention have been described herein with reference to the accompanying drawings, it is to be understood that the invention is not limited to those precise embodiments, and that various other changes and modifications may be affected therein by one skilled in the art without departing from the scope and spirit of the invention.

What is claimed is:

1. A method for use in a remote terminal for improving access latency in a random access channel in a communications system including at least one base station, the method comprising the steps of:

selecting a time duration associated with an access signal for transmission, the time duration being selected from among time durations which range from being substantially equivalent to a length of a transmission frame of the base station to being less than the length of the transmission frame; and transmitting the access signal having the selected time duration associated therewith to the base station over the random access channel in a selected time offset slot associated with the channel.

2. The method of claim 1, wherein the transmission frame length is about ten milliseconds.

3. The method of claim 1, wherein the time duration of a message portion of the access signal is one of about five millisecond or about ten milliseconds.

4. The method of claim 1, wherein the communications system is a UMTS.

5. The method of claim 1, wherein the random access channel is a logical channel of a media access control layer associated with the communications system.

6. The method of claim 1, further comprising the step of indicating to the base station the selected time duration prior to transmission of the access signal.

7. The method of claim 1, wherein the access signal includes an access request.

8. The method of claim 1, wherein the access signal includes a data packet.

9. Apparatus for improving access latency in a random access channel in a communications system including at least one base station, comprising:
   a remote terminal configured for selecting a time duration associated with an access signal, the time duration being selected from among time durations which range from being substantially equivalent to a length of a transmission frame of the base station to being less than the length of the transmission frame, the remote terminal also configured for transmitting the access signal having the selected time duration associated therewith to the base station over the random access channel in a selected time offset slot associated with the channel.

10. The apparatus of claim 9, wherein the transmission frame length is about ten milliseconds.

11. The apparatus of claim 9, wherein the time duration of a message portion of the access signal is one of about five millisecond or about ten milliseconds.

12. The apparatus of claim 9, wherein the communications system is a UMTS.

13. The apparatus of claim 9, wherein the random access channel is a logical channel of a media access control layer associated with the communications system.

14. The apparatus of claim 9, wherein the remote terminal is further configured for indicating to the base station the selected time duration prior to transmission of the access signal.

15. The apparatus of claim 9, wherein the access signal includes an access request.

16. The apparatus of claim 9, wherein the access signal includes a data packet.

17. A method for use in a base station for improving access latency in a random access channel in a communications system including at least one remote terminal, the method comprising the steps of:
   selecting a transmission frame time duration associated with a random access channel, the transmission frame time duration being selected from among one or more supported time durations; and
   acknowledging a successful access signal transmitted by the remote terminal over the random access channel in a selected time offset slot associated with the channel.

18. The method of claim 17, wherein the transmission frame time duration is one of about five millisecond or about ten milliseconds.

19. The method of claim 17, wherein a time duration of a message portion of the access signal is one of about five millisecond or about ten milliseconds.

20. The method of claim 17, wherein the communications system is a UMTS.

21. The method of claim 17, wherein the random access channel is a logical channel of a media access control layer associated with the communications system.

22. The method of claim 17, further comprising the step of indicating to the remote terminal the selected transmission frame time duration.

23. The method of claim 17, wherein the access signal includes an access request.

24. The method of claim 17, wherein the access signal includes a data packet.

25. Apparatus for improving access latency in a random access channel in a communications system including at least one remote terminal, comprising:
   a base station configured for selecting a transmission frame time duration associated with a random access channel, the transmission frame time duration being selected from among one or more supported time durations, the base station also configured for acknowledging a successful access signal transmitted by the remote terminal over the random access channel in a selected time offset slot associated with the channel.

26. The apparatus of claim 25, wherein the transmission frame time duration is one of about five millisecond or about ten milliseconds.

27. The apparatus of claim 25, wherein a time duration of a message portion of the access signal is one of about five millisecond or about ten milliseconds.

28. The apparatus of claim 25, wherein the communications system is a UMTS.

29. The apparatus of claim 25, wherein the random access channel is a logical channel of a media access control layer associated with the communications system.

30. The apparatus of claim 25, wherein the base station is further configured for indicating to the remote terminal the selected transmission frame time duration.

31. The apparatus of claim 25, wherein the access signal includes an access request.

32. The apparatus of claim 25, wherein the access signal includes a data packet.

33. The method of claim 1, wherein the length of the transmission frame is selected by the base station from among one or more supported time durations.

34. The method of claim 33, wherein the remote terminal receives an indication of the selected transmission frame length from the base station.

35. The apparatus of claim 9, wherein the length of the transmission frame is selected by the base station from among one or more supported time durations.

36. The apparatus of claim 35, wherein the remote terminal receives an indication of the selected transmission frame length from the base station.

* * * * *